US007163907B1

(12) United States Patent
Canich et al.

(10) Patent No.: US 7,163,907 B1
(45) Date of Patent: Jan. 16, 2007

(54) ALUMINUM-FREE MONOCYCLOPENTADIENYL METALLOCENE CATALYSTS FOR OLEFIN POLYMERIZATION

(75) Inventors: Jo Ann Marie Canich, Webster, TX (US); Howard William Turner, Webster, TX (US); Gregory George Hlatky, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 07/542,236

(22) Filed: Jun. 22, 1990

Related U.S. Application Data

(63) Continuation-in-part of application No. 07/533,245, filed on Jun. 4, 1990, now Pat. No. 5,055,438, which is a continuation-in-part of application No. 07/406,945, filed on Sep. 13, 1989, now abandoned, and a continuation-in-part of application No. 07/133,480, filed on Dec. 22, 1987, and a continuation-in-part of application No. 07/133,052, filed on Dec. 21, 1987, now abandoned, which is a continuation-in-part of application No. 07/008,800, filed on Jan. 30, 1987, now abandoned, and a continuation-in-part of application No. 07/011,471, filed on Jan. 30, 1987, now abandoned.

(51) Int. Cl.
    *B01J 31/00* (2006.01)
(52) U.S. Cl. .................................. 502/152; 502/155
(58) Field of Classification Search ............... 502/103, 502/114, 115, 116, 117, 118, 121, 123, 124, 502/126, 155, 154, 152, 153; 526/113, 114
See application file for complete search history.

(56) References Cited

U.S. PATENT DOCUMENTS

| | | | | |
|---|---|---|---|---|
| 4,701,432 A | * | 10/1987 | Welborn, Jr. ............... 502/113 |
| 4,791,180 A | | 12/1988 | Turner ....................... 526/160 |
| 5,064,802 A | * | 11/1991 | Stevens et al. ......... 502/103 X |
| 5,066,741 A | * | 11/1991 | Campbell, Jr. ............. 526/171 |
| 5,132,380 A | * | 7/1992 | Stevens et al. ............. 526/126 |
| 5,198,401 A | * | 3/1993 | Turner et al. ............... 502/155 |
| 5,214,173 A | * | 5/1993 | Jordan et al. .................. 556/8 |
| 5,241,025 A | * | 8/1993 | Hlatky et al. .............. 526/129 |
| 5,264,405 A | * | 11/1993 | Canich ....................... 502/103 |
| 5,278,119 A | * | 1/1994 | Turner et al. ............... 502/155 |
| 5,321,106 A | * | 6/1994 | LaPointe ................... 526/126 |
| 5,384,299 A | * | 1/1995 | Turner et al. ............... 502/155 |
| 5,407,884 A | * | 4/1995 | Turner et al. ............... 502/155 |
| 5,408,017 A | * | 4/1995 | Turner et al. ............... 526/134 |
| 5,470,927 A | * | 11/1995 | Turner et al. ............... 526/126 |
| 5,483,014 A | * | 1/1996 | Turner et al. ............... 526/113 |
| 5,502,124 A | * | 3/1996 | Crowther et al. ........... 526/127 |
| 5,504,049 A | * | 4/1996 | Crowther et al. ........... 502/117 |
| 5,504,169 A | * | 4/1996 | Canich ....................... 526/127 |
| 5,599,761 A | * | 2/1997 | Turner ....................... 502/152 |
| 5,621,126 A | * | 4/1997 | Canich et al. ................. 556/9 |
| 5,801,113 A | * | 9/1998 | Jejelowo et al. ............ 502/104 |
| 6,121,395 A | * | 9/2000 | Turner ....................... 526/134 |

(Continued)

FOREIGN PATENT DOCUMENTS

EP 277003 * 8/1988 ................ 502/117

(Continued)

OTHER PUBLICATIONS

Jordan et al, JACS, 1986, 108, pp. 7410-7411.*

(Continued)

*Primary Examiner*—J. Pasterczyk
(74) *Attorney, Agent, or Firm*—Catherine L. Bell; Myron B. Kurtzman

(57) ABSTRACT

This invention relates to a catalyst system for the production of polyolefins comprising:

(A) a Group IV B transition metal component represented by one of the two general formulae

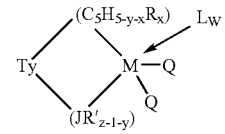

wherein $(C_5H_{5-y-x}R_x)$ is a cylopentadienyl ring $(JR'_{z-1-y})$ is a heteroatom ligand in which J is an element with a coordination number of three from Group V-A or an element with a coordination number of two rom Group VI-A of the Periodic Table of Elements, each Q is independently, hydride, $C_1$—$C_{20}$ hydrocarbyl radicals, substituted hydrocarbyl radials wherein one or more hydrogen atoms is replaced by an electron withdrawing group, or $C_1$—$C_{20}$ hydrocarbyl-substituted metalloid radicals wherein the metalloid is selected from the group consisting of germanium and silicon, provided that Q is not a substituted or unsubstituted cyclopentadienyl ring, or both Q together may be an alkylidene, olefin, acetylene or a cyclometallated hydrocarbyl;

"y" is 0 or 1; when "y" is 1, T is a covalent bridging group containing a Group IV-A or V-A element;

L is a neutral Lewis base; and "w" is a number from 0 to 3;

(B) an activator compound comprising (1) a cation; and (2) a compatible noncoordinating anion.

52 Claims, No Drawings

U.S. PATENT DOCUMENTS

| | | | | |
|---|---|---|---|---|
| 6,160,066 A | * | 12/2000 | Canich | 526/160 |
| 6,232,420 B1 | * | 5/2001 | Turner | 526/348.6 |
| 6,245,706 B1 | * | 6/2001 | Hlatky | 502/152 |
| 6,265,338 B1 | * | 7/2001 | Canich | 502/103 |
| 6,355,592 B1 | * | 3/2002 | Hlatky et al. | 502/103 |
| 6,423,795 B1 | * | 7/2002 | Canich et al. | 526/160 |
| 6,617,466 B1 | * | 9/2003 | Canich | 556/11 |

FOREIGN PATENT DOCUMENTS

| | | | | |
|---|---|---|---|---|
| EP | 277004 | * | 8/1988 | 502/117 |
| EP | 0418044 A2 | | 3/1991 | |
| WO | WO 87/03887 | * | 7/1987 | 502/117 |
| WO | 9102012 | | 2/1991 | |

OTHER PUBLICATIONS

Jordan et al, JACS, 1986, 108, pp. 1718-1719.*
Zambelli et al, *Macromolecules*, 1989, 22, pp. 2186-2189.*
Shapiro et al, Organometallies 1990, 9, 867-869.*
Oruda, Chem. Ber. 123 (1990), 1649-1651.*
US RE37,788 E, Canich, Jul. 2002, US class 556/9.*
Chemical and Engineering News, vol. 63, No. 5, p. 27, 1985.*
J. Bercaw et al. Southwest Regional ACS Meeting, Corpus Christi, TX, Nov. 30, 1988 (Abstract #47).
Zerlong Lin et al. J.Am.Chem.Soc., 1987, 109, 4127-4129.
G. Hlatky et al. J.Am.Chem.Soc., 1989, 111, 2728-2729.
G. Schmidt et al. J.Am.Chem.Soc., 1985, 107, 1443-1444.
R. Cracknell et al., J.Chem.Soc., Chem.Commun., 1984, 326-328.
M. Brookhart et al., J.Organometallics Chem., 250 (1983) 395-408.
M. Brookhart et al., J.Chem.Soc., Chem. Commun., 1983, 691-693.
M. Reetz, *Organotitanium Reagents in Organic Synthesis*, pp. 117 and 121 (Springer-Verlay 1986.
Kukenhohner, "Untersuchungen zur Darstellung Chiraler Organotitan (IV)—Verbindungen fur Enantioselektire Synthesen" (1983) (unpublished Diplomarbeit, University of Marburg, Germany).
KukenHohner, Organotitan (IV) Agentien: Komplexe Chiraler Chelatiganden und Enantioselektire c-c- Verknupfungen (University of Marburg, Germany 1986).

* cited by examiner

ALUMINUM-FREE MONOCYCLOPENTADIENYL METALLOCENE CATALYSTS FOR OLEFIN POLYMERIZATION

This application is a continuation-in-part of U.S. patent application Ser. No. 07/533,245, filed Jun. 4, 1990, now U.S. Pat. No. 5,055,438 issued Oct. 8, 1991, which is a continuation-in-part of U.S. patent application Ser. No. 07/406,945, filed Sep. 13, 1989, now abandoned, and is a continuation-in-part of U.S. patent application Ser. No. 07/133,480, filed Dec. 22, 1987, which is a continuation-in-part of U.S. patent application Ser. No. 07/008,800, filed Jan. 30, 1987, now abandoned, and is a continuation-in-part of U.S. patent application Ser. No. 07/133,052, filed Dec. 21, 1987 an now abandoned, which is a continuation-in-part of U.S. patent application Ser. No. 07/011,471, filed Jan. 30, 1987 and now abandoned.

FIELD OF THE INVENTION

This invention relates to certain transition metal compounds of the Group IV-B metals of the Periodic Table of Elements, to a catalyst system comprising such Group IV-B transition metal compounds and an ion-exchange activator compound, and to a process using such catalyst system for the production of polyolefins, particularly polyethylene, polypropylene, and ethylene-α-olefin copolymers.

BACKGROUND OF THE INVENTION

As is well known, various processes and catalysts exist for the homopolymerization or copolymerization of olefins. Traditional Ziegler-Natta catalyst systems—a transition metal compound cocatalyzed by an aluminum alkyl—are capable of producing polyolefins having a high molecular weight but a broad molecular weight distribution. Traditional types of Ziegler-Natta catalysts have very high activities, and the polyolefins produced therewith have low catalyst residues and do not require a subsequent catalyst residue deashing treatment.

More recently a "metallocene" type catalyst system has been developed—one wherein the transition metal compound has cyclopentadienyl ring ligands, preferably at least two; such transition metal compound being referred to as a "metallocene"—which catalyzes the production of olefin monomers to polyolefins. Accordingly, metallocene compounds of the Group IV-B-metals, particularly bis(cyclopentadienyl) titanocenes and zirconocenes, have been utilized as the transition metal component in such "metallocene" containing catalyst system for the production of polyolefins and ethylene-α-olefin copolymers. When such metallocenes are cocatalyzed with an aluminum alkyl—as is the case with a traditional type Ziegler-Natta catalyst system—the catalytic activity of such metallocene catalyst system is generally too low to be of any commercial interest.

It has since become known that such metallocenes may be cocatalyzed with an alumoxane—rather than an aluminum alkyl—to provide a metallocene catalyst system of high activity for catalyzing the production of moderately high molecular weight polyolefins. Unfortunately, the amount of alumoxane cocatalyst required to provide the metallocene component with high activity is generally high, generally expressed as a molar ratio of Al to transition metal, hence a polyolefin produced from such metallocene-alumoxane catalyst may contain an undesirable amount of catalyst residue (or ash content, measured as the nonvolatile aluminum and transition metal content).

More recently, a new method of activating Group IV-B metallocene alkyl complexes was disclosed in European Patent Applications Nos. 277,003 and 277,004. The improved metallocene catalysts are prepared by combining at least two components. The first component is a bis (cyclopentadienyl) derivative of a Group IV-B metal containing at least one ligand which will combine with the cationic portion of the second component. The second component is an ion-exchange reagent comprising a cation which will irreversibly react with at least one ligand contained in said Group IV-B metal compound (first component) and a non-coordinating anion which is bulky, labile and stable. Suitable non-coordinating anions disclosed in these applications include: 1) anionic coordination complexes comprising a plurality of lipophilic radicals covalently coordinated to and shielding a central charge-bearing metal or metalloid core, and 2) anions comprising a plurality of boron atoms such as carboranes, metallocarboranes and boranes. Upon combination of the first and second components, the cation of the second component reacts with one of the ligands of the first component, thereby generating an ion-pair consisting of a Group IV-B metallocene cation with a formal coordination number of 3 and a valence of 4+ and the aforementioned non-coordinating anion. The disclosures are limited to catalyst systems derived from Group IV-B metallocene complexes containing at least two cyclopentadienyl ligands.

Aluminum alkyl-free olefin polymerization catalysts derived from transition metal complexes containing fewer than two cyclopentadienyl ligands have been relatively unexplored. John Bercaw reported [Organometallics, 1990, 9, 867] the synthesis of a monocyclopentadienyl scandium polymerization catalyst, $[Me_2Si(C_5Me_4)(N-Bu^t)ScH(PMe_3)]_2$. This neutral Group III catalyst has a low activity and is very expensive due to the high cost of scandium metal. The need exists to provide a method of preparing highly active, versatile, aluminum alkyl-free olefin polymerization catalysts derived from monocyclopentadienyl ligand systems.

SUMMARY OF THE INVENTION

The catalyst system of this invention comprises a transition metal component from Group IV B of the Periodic Table of the Elements (CRC Handbook of Chemistry and Physics, 68th ed. 1987–1988) and an ion-exchange reagent which may be employed in solution, slurry, gas phase or bulk phase polymerization procedure to produce a polyolefin of high weight average molecular weight and relatively narrow molecular weight distribution.

In general the Group IV B transition metal component can be a polyalkyl or hydride complex containing fewer than two cyclopentadienyl groups.

The "Group IV B transition metal component" of the mono-cyclopentadienyl catalyst system is represented by the general formula:

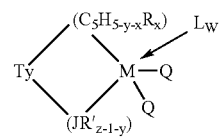

wherein: M is Zr, Hf or Ti and is in its highest formal oxidation state (+4, d⁰ complex);

$(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen atom, $C_1$–$C_{20}$ hydrocarbyl-substituted metalloid radicals wherein the metalloid is selected from the Group IV A of the Periodic Table of Elements, and halogen radicals; or $(C_5H_{5-y-x}R_x)$ is a cyclopentadienyl ring in which two adjacent R-groups are joined forming a $C_4$–$C_{20}$ ring to give a polycyclic cyclopentadienyl ligand such as indenyl and fluorenyl derivatives.

$(JR'_{x-l-y})$ is a heteroatom ligand in which J is an element with a coordination number of three from Group V A or an element with a coordination number of two from Group VI A of the Periodic Table of Elements, preferably nitrogen, phosphorus, oxygen or sulfur, and each R' is, independently a radical selected from a group consisting of $C_1$–$C_{20}$ hydrocarbyl radicals, substituted $C_1$–$C_{20}$ hydrocarbyl radicals wherein one or more hydrogen atoms is replaced by a halogen atom, and "z" is the coordination number of the element J;

each Q may be independently, hydride, $C_1$–$C_{50}$ hydrocarbyl radicals, substituted hydrocarbyl radicals wherein one or more hydrogen atoms is replaced by an electron-withdrawing group such as a halogen atom, or alkoxide radical, or $C_1$–$C_{50}$ hydrocarbyl-substituted metalloid radicals wherein the metalloid is selected from the Group IV-A of the Period Table of Elements, provided that were any Q is a hydrocarbyl such Q is different from $(C_5H_{5-y-x}R_x)$, or both Q together may be an alkylidene, olefin, acetylene or a cyclometallated hydrocarbyl.

"y" is 0 or 1; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like;

L is a neutral Lewis base such as diethylether, tetrahydrofuran, dimethylaniline, aniline, trimethylphosphine, n-butylamine, and the like; and "w" is a number from 0 to 3; L can also be a second transition metal compound of the same type such that the two metal centers M and M' are bridged by Q and Q', wherein M' has the same meaning as M and Q' has the same meaning as Q. Such compounds are represented by the formula:

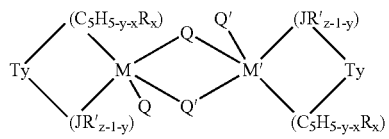

The second component is an ion-exchange compound comprising a cation which will irreversibly react with at least one ligand contained in said Group IV-B metal compound and a noncoordinating anion which is bulky, labile, and stable. Upon combination of the first and second components, the cation of the second component reacts with one of the ligands of the first component, thereby generating an ion pair consisting of a Group IV-B metal cation with a formal coordination number of 3 and a valence of +4 and the aforementioned anion, which anion is compatible with and non-coordinating toward the metal cation formed from the first component. Illustrative but not limiting examples of cations of the second component include Bronsted acids such as ammonium ions or reducible Lewis acids such as Ag⁺ or ferrocenium ions. The anion of the second compound must be capable of stabilizing the Group IV-B metal cation complex without interfering with the Group IV-B metal cation's or its decomposition product's ability to function as a catalyst and must be sufficiently labile to permit displacement by an olefin, diolefin or an acetylenically unsaturated monomer during polymerization.

Catalyst systems of the invention may be prepared by placing the "Group IV B transition metal component" and the ion-exchange component in common solution in a normally liquid alkane or aromatic solvent, which solvent is preferably suitable for use as a polymerization diluent for the liquid phase polymerization of an olefin monomer. Suitable catalysts can also be prepared by reacting the components and adsorbing on a suitable support material (inorganic oxides or polymers, for example) or by allowing the components to react on such support.

A typical polymerization process of the invention such as for the polymerization or copolymerization of ethylene comprises the steps of contacting ethylene alone, or with other unsaturated monomers including $C_3$–$C_{20}$ α-olefins, $C_5$–$C_{20}$ diolefins, and/or acetylenically unsaturated monomers either alone or in combination with other olefins and/or other unsaturated monomers, with a catalyst comprising, in a suitable polymerization diluent, the Group IV B transition metal component illustrated above; and the ion-exchange activator component in an amount to provide a molar transition metal to activator ratio of from about 1:10 to about 200:1 or more; and reacting such monomer in the presence of such catalyst system at a temperature of from about −100° C. to about 300° C. for a time of from about 1 second to about 10 hours to produce a polyolefin having a weight average molecular weight of from about 1,000 or less to about 5,000,000 or more and a molecular weight distribution of about 1.5 or greater.

DESCRIPTION OF THE PREFERRED EMBODIMENT

Ionic Catalyst System—General Description

The process of this invention is practiced with that class of ionic catalysts prepared by combining at least two components. The first of these is a monocyclopentadienyl derivative of a Group IV-B metal compound containing at least one ligand which will combine with the second component or at least a portion thereof such as the cation portion thereof. The second component is an ion-exchange compound comprising a cation which will irreversibly react with at least one ligand contained in said Group IV-B metal compound and a noncoordinating anion which is bulky, labile, and stable. Upon combination of the first and second components, the cation of the second component reacts with one of the ligands of the first component, thereby generating an ion pair consisting of a Group IV-B metal cation with a formal coordination number of 3 when w is zero and a valence of +4 and the aforementioned anion, which anion is compatible with and non-coordinating towards the metal cation formed from the first component. The anion of the second compound must be capable of stabilizing the Group IV-B metal cation complex without interfering with the Group IV-B metal cation's or its decomposition product's ability to function as a catalyst and must be sufficiently labile to permit displacement by an olefin, diolefin or an acetylenically unsaturated monomer during polymerization.

A. Catalyst Component

The Group IV-B transition metal component of the catalyst system is represented by the general formula:

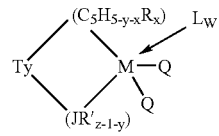

wherein: M is Zr, Hf or Ti and is in its highest formal oxidation state (+4, $d^0$ complex);

$(C_5H_{5-y-x}R_x)$ is a cyclopentadienyl ring which is substituted with from zero to five substituent groups R, "x" is 0, 1, 2, 3, 4 or 5 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen atom, $C_1$–$C_{20}$ hydrocarbyl-substituted metalloid radicals wherein the metalloid is selected from the Group IV A of the Periodic Table of Elements, and halogen radicals; or $(C_5H_{5-y-x}R_x)$ is a cyclopentadienyl ring in which two adjacent R-groups are joined forming a $C_4$–$C_{20}$ ring to give a polycyclic cyclopentadienyl ligand such as indenyl and fluorenyl derivatives;

$(JR'_{z-1-y})$ is a heteroatom ligand in which J is an element with a coordination number of three from Group V A or an element with a coordination number of two from Group VI A of the Periodic Table of Elements, preferably nitrogen, phosphorus, oxygen or sulfur with nitrogen being preferred, and each R' is, independently a radical selected from a group consisting of $C_1$–$C_{20}$ hydrocarbyl radicals, substituted $C_1$–$C_{20}$ hydrocarbyl radicals wherein one or more hydrogen atoms is replaced by a halogen atom, and "z" is the coordination number of the element J;

each Q may be independently, hydride, $C_1$–$C_{50}$ hydrocarbyl radicals, substituted hydrocarbyl radicals wherein one or more hydrogen atoms is replaced by an electron-withdrawing group such as a halogen atom, or alkoxide radical, or $C_1$–$C_{50}$ hydrocarbyl-substituted metalloid radicals wherein the metalloid is selected from the Group IV-A of the Periodic Table of Elements, provided that where any Q is a hydrocarbyl such Q is different from $(C_5H_{5-y-x}R_x)$, or both Q together may be an alkylidene olefin, acetylene or a cyclometallated hydrocarbyl;

"y" is 0 or 1; when "y" is 1, T is a covalent bridging group containing a Group IV A or V A element such as, but not limited to, a dialkyl, alkylaryl or diaryl silicon or germanium radical, alkyl or aryl phosphine or amine radical, or a hydrocarbyl radical such as methylene, ethylene and the like. Examples of the T group which are suitable as a constituent group of the Group IV B transition metal component of the catalyst system are identified in Column 1 of Table 1 under the heading "T".

L is a neutral Lewis base such as diethylether, tetrahydrofuran, dimethylaniline, aniline, trimethylphosphine, n-butylamine, and the like; and "w" is a number from 0 to 3; L can also be a second transition metal compound of the same type such that the two metal centers M and M' are bridged by Q and Q', wherein M' has the same meaning as M and Q' has the same meaning as

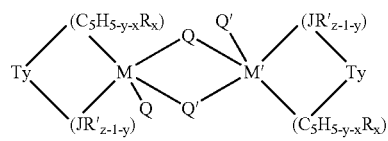

Exemplary hydrocarbyl radicals for the Q are methyl, ethyl, propyl, butyl, amyl, isoamyl, hexyl, isobutyl, heptyl, octyl, nonyl, decyl, cetyl, 2-ethylhexyl, phenyl and the like, with methyl being preferred. Exemplary substituted hydrocarbyl radicals include trifluoromethyl, pentafluorphenyl, trimethylsilylmethyl, and trimethoxysilylmethyl and the like. Exemplary hydrocarbyl substituted metalloid radicals include trimethylsilyl, trimethylgermyl, triphenylsilyl, and the like. Exemplary alkyldiene radicals for both Q together are methylidene, ethylidene and propylidene. Examples of the Q group which are suitable as a constituent group or element of the Group IV B transition metal component of the catalyst system are identified in Column 4 of Table 1 under the heading "Q".

Suitable hydrocarbyl and substituted hydrocarbyl radicals, which may be substituted as an R group for at least one hydrogen atom in the cyclopentadienyl ring, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals. Suitable organometallic radicals, which may be substituted as an R group for at least one hydrogen atom in the cyclopentadienyl ring, include trimethylsilyl, triethylsilyl, ethyldimethylsilyl, methyldiethylsilyl, triphenylgermyl, trimethylgermyl and the like. Examples of cyclopentadienyl ring groups ($C_5H_{5-y-x}R_x$) which are suitable as a constituent group of the Group IV B transition metal component of the catalyst system are identified in Column 2 of Table 1 under the heading ($C_5H_{5-y-x}R_x$) Suitable hydrocarbyl and substituted hydrocarbyl radicals, which may be used as an R' group in the heteroatom J ligand group, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals. Examples of heteroatom ligand groups ($JR'_{z-1-y}$) which are suitable as a constituent group of the Group IV B transition metal component of the catalyst system are identified in Column 3 of Table 1 under the heading ($JR'_{z-1-y}$).

Table 1 depicts representative constituent moieties for the "Group IV B transition metal component", the list is for illustrative purposes only and should not be construed to be limiting in any way. A number of final components may be formed by permuting all possible combinations of the constituent moieties with each other. Illustrative compounds are: dimethylsilyltetramethylcyclopentadienyl-tert-butylamido zirconium dimethyl, dimethylsilyltetramethylcyclopentadienyl-tert-butylamido hafnium diethyl, dimethylsilyl-tert-butylcyclopentadienyl-tert-butyl-amido zirconium dihydride, dimethylsilyl-tert-butylcyclopentadienyl-tert-butylamido hafnium diphenyl, dimethylsilyltrimethylsilyl-cyclopentadienyl-tert-butylamido zirconium dihydride, dimethylsilyltetramethylcyclopentadienylphenylamido titanium dimethyl, dimethylsilyltetramethylcyclopentadienylphenylamido hafnium ditolyl, methylphenyl-silyltetramethylcyclopentadienyltert-butylamido zirconium dihydride, methylphenylsilyltetramethylcyclopentadienyl-tert-butylamido hafnium dimethyl, dimethylsilylfluorenyl-cyclohexylamido titanium dimethyl, diphenylgermylindenyl-t-butyl phosphido titanium dihydride methylphenylsilyltetramethylcyclopentadienyl-tert-butylamido hafnium dimethyl, dimethylsilyltetramethylcyclopentadienyl-p-n-butylphenylamido zirconium dihydride, dimethylsilyltetramethyl-ocyclopentadienyl-p-n-butylphenylamido hafnium dihydride. For illustrative purposes, the above compounds and those permuted from Table 1 do not include the neutral Lewis base ligand (L). The conditions under which complexes containing neutral Lewis base ligands such as ether or those which form dimers is determined by the steric bulk of the ligands about the metal center. Similarly, due to the decreased steric bulk of the trimethylsilylcyclopentadienyl group in $[Me_2Si(Me_3SiC_5H_3)(N\text{-t-Bu})ZrH_2]_2$ versus that of the tetramethyl-cyclopentadienyl group in $Me_2Si(Me_4C_5)(N\text{-t-Bu})\text{-}ZrH_2$, the former compound is dimeric and the latter is not.

Generally the bridged species of the Group IV B transition metal compound ("y"=1) are preferred. A preferred method of preparing these compounds is by reacting a cyclopentadienyl lithium compound with a dihalo-compound whereupon a lithium halide salt is liberated and a monohalo substituent becomes covalently bound to the cyclopentadienyl compound. The so substituted cyclopentadienyl reaction product is next reacted with a lithium salt of a phosphide, oxide, sulfide or amide (for the sake of illustration, a lithium amide) whereupon the halo element of the monohalo substituent group of the reaction product reacts to liberate a lithium halide salt and the amine moiety of the lithium amide salt becomes covalently bound to the substituent of the cyclopentadienyl reaction product. The resulting amine derivative of the cyclopentadienyl product is then reacted with an alkyl lithium reagent whereupon the labile hydrogen atoms, at the carbon atom of the cyclopentadienyl compound and at the nitrogen atom of the amine moiety covalently bound to the substituent group, react with the alkyl of the lithium alkyl reagent to liberate the alkane and produce a dilithium salt of the cyclopentadienyl compound. Thereafter the bridged species of the Group IV B transition metal compound is produced by reacting the dilithium salt cyclopentadienyl compound with a Group IV B transition metal preferably a Group IV B transition metal halide. This procedure yields the dichloro-derivative of the monocyclopentadienyl-amido Group IV-B compound. The dichloride complex is then converted into the appropriate hydrocarbyl derivative using the corresponding Grignard, lithium, sodium or potassium salt of the hydrocarbyl ligand. The procedures used are analogous to those developed for alkylating the Group IV-B metallocene complexes (i.e., the bis-cyclopentadienyl systems).

TABLE 1

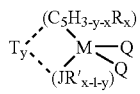

| T (when y = 1) | $(C_5H_{3-y-x}R_x)$ | $(JR'_{x-1-y})$ | Q | M |
|---|---|---|---|---|
| dimethylsilyl | cyclopentadienyl | t-butylamide | hydride | zirconium |
| diethylsilyl | methylcyclopentadienyl | phenylamide | methyl | hafnium |
| di-n-propylsilyl | 1,2-dimethylcyclopentadienyl | p-n-butylphenylamide | ethyl | titanium |
| diisopropylsilyl | 1,3-dimethylcyclopentadienyl | cyclohexylamide | phenyl | |
| di-n-butylsilyl | indenyl | perflurophenylamide | n-propyl | |
| di-t-butylsilyl | 1,2-diethylcyclopentadienyl | n-butylamide | isopropyl | |
| di-n-hexylsilyl | tetramethylcyclopentadienyl | methylamide | n-butyl | |
| methylphenylsilyl | ethylcyclopentadienyl | ethylamide | amyl | |
| ethylmethylsilyl | n-butylcyclopentadienyl | n-propylamide | isoamyl | |
| diphenylsilyl | cyclohexylmethylcyclopentadienyl | isopropylamide | hexyl | |
| di(p-t-butylphenethylsilyl) | n-octylcyclopentadienyl | benzylamido | isobutyl | |
| n-hexylmethylsilyl | β-phenylpropylcyclopentadienyl | t-butylphosphide | heptyl | |
| cyclopentamethylenesilyl | tetrahydroindenyl | ethylphosphide | actyl | |
| cyclotetramethylenesilyl | propylcyclopentadienyl | phenylphosphide | nonyl | |
| cyclotrimethylenesilyl | t-butylcyclopentadienyl | cyclohexylphosphide | decyl | |
| dimethylgermanyl | benzylcyclopentadienyl | oxo (when y = 1) | cetyl | |
| diethylgermanyl | diphenylmethylcyclopentadienyl | sulfide (when y = 1) | methylidene (both Q) | |
| phenylamide | trimethylgermylcyclopentadienyl | methoxide (when y = 0) | ethylidene (both Q) | |
| t-butylamide | trimethylstearylcyclopentadienyl | ethoxide (when y = 0) | propylidene (both Q) | |
| methylamide | triethylplumbylcyclopentadienyl | methylthio (when y = 0) | | |
| t-butylphosphide | trifluromethylcyclopentadienyl | ethylthio (when y = 0) | | |
| ethylphosphide | trimethylsilylcyclopentadienyl | | | |
| phenylphosphide | pentamethylcyclopentadienyl (when y = 0) | | | |
| methylene | fluorenyl | | | |
| dimethylmethylene | methylfluorenyl | | | |
| diethylmethylene | octahydrofluorenyl | | | |
| ethylene | | | | |
| dimethylethylene | | | | |
| diethylethylene | | | | |
| dipropylethylene | | | | |
| propylene | | | | |
| dimethylpropylene | | | | |
| diethylpropylene | | | | |
| 1,1-dimethyl-3,3-dimethylpropylene | | | | |
| tetramethyldisiloxane | | | | |
| 1,1,4,4-tetramethyldisilylethylene | | | | |

Unbridged species of the Group IV B transition metal compound can be prepared from the reaction of a cyclopentadienyl lithium compound and a lithium salt of an amine with a Group IV B transition metal halide.

Suitable, but not limiting, Group IV B transition metal compounds which may be utilized in the catalyst system of this invention include those bridged species ("y"=1) wherein the T group bridge is a dialkyl, diaryl or alkylaryl silane, or methylene or ethylene. Examples of the more preferred species of bridged Group IV B transition metal compounds are dimethylsilyl, methylphenylsilyl, diethylsilyl, ethylphenylsilyl, diphenylsilyl, ethylene or methylene bridged compounds. Most preferred of the bridged species are dimethylsilyl, diethylsilyl and methylphenylsilyl bridged compounds.

Suitable Group IV B transition metal compounds which are illustrative of the unbridged ("y"=0) species which may be utilized in the catalyst systems of this invention are exemplified by pentamethylcyclopentadienyldi-t-butylphosphinohafnium dimethyl; pentamethylcyclopentadienyldi-t-butylphosphinohafnium methylethyl; cyclopentadienyl-2-methylbutoxide titanium dimethyl.

To illustrate members of the Group IV B transition metal component, select any combination of the species in Table 1. An example of a bridged species would be dimethylsilylcyclopentadienyl-t-butylamidozirconium; an example of an unbridged species would be cyclopentadienylide-t-butylamidozirconium dihydride.

B. The Activator Component

Compounds useful as an activator component in the preparation of the catalyst of this invention will comprise a cation, which is a Bronsted acid capable of donating a proton, and a compatible noncoordinating anion which anion is relatively large (bulky), capable of stabilizing the active catalyst species (the Group IV-B cation) which is formed when the two compounds are combined and said anion will be sufficiently labile to be displaced by olefinic, diolefinic and acetylenically unsaturated substrates or other neutral Lewis bases such as ethers, nitrites and the like. Two classes of compatible non-coordinating anions have been disclosed in our European Patent Applications 277,003 and 277,004:1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In general, the activator compounds containing single anionic coordination complexes which are useful in this invention may be represented by the following general formula:

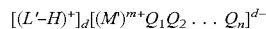   5.

Wherein:
L' is a neutral Lewis base;
H is a hydrogen atom;
[L'-H] is a Bronsted acid;
M' is a metal or metalloid selected from the Groups subtended by Groups V-B to V-A of the Periodic Table of the Elements; i.e., Groups V-B, VI-B, VII-B, VIII, I-B, II-B, III-A, IV-A, and V-A;
$Q_1$ to $Q_n$ are selected, independently, from the Group consisting of hydride radicals, dialkylamido radicals, alkoxide and aryloxide radicals, hydrocarbyl and substituted-hydrocarbyl radicals and organometalloid radicals and any one, but not more than one, of $Q_1$ to $Q_n$ may be a halide radical, the remaining $Q_1$ to $Q_n$ being, independently, selected from the foregoing radicals;
m is an integer from 1 to 7;
n is an integer from 2 to 8; and n−m=d.

As indicated above, any metal or metalloid capable of forming an anionic complex which is stable in water may be used or contained in the anion of the second compound. Suitable metals, then, include, but are not limited to, aluminum, gold, platinum and the like. Suitable metalloids include, but are not limited to, boron, phosphorus, silicon and the like. Compounds containing anions which comprise coordination complexes containing a single metal or metalloid atom are, of course, well known and many, particularly such compounds containing a single boron atom in the anion portion, are available commercially. In light of this, salts containing anions comprising a coordination complex containing a single boron atom are preferred.

The preferred activator compounds comprising boron may be represented by the following general formula:

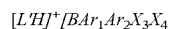   5A.

Wherein:
L' is a neutral Lewis base;
H is a hydrogen atom;
[L'-H]⁺ is a Bronsted acid;
B is boron in a valence state of 3;
$Ar_1$ and $Ar_2$ are the same or different aromatic or substituted-aromatic hydrocarbon radicals containing from about 6 to about 20 carbon atoms and may be linked to each other through a stable bridging group; and
$X_3$ and $X_4$ are radicals selected, independently, from the group consisting of hydride radicals, halide radicals, with the proviso that $X_3$ and $X_4$ will not be halide at the same time, hydrocarbyl radicals containing from 1 to about 20 carbon atoms, substituted-hydrocarbyl radicals, wherein one or more of the hydrogen atoms is replaced by a halogen atom, containing from 1 to about 20 carbon atoms, hydrocarbyl-substituted metal (organometalloid) radicals wherein each hydrocarbyl substitution contains from 1 to about 20 carbon atoms and said metal is selected from Group IV-A of the Periodic Table of the Elements and the like.

In general, $Ar_1$ and $Ar_2$ may, independently, be any aromatic or substituted-aromatic hydrocarbon radical containing from about 6 to about 20 carbon atoms. Suitable aromatic radicals include, but are not limited to, phenyl, naphthyl and anthracenyl radicals. Suitable substituents on the substituted-aromatic hydrocarbon radicals, include, but are not necessarily limited to, hydrocarbyl radicals, organometalloid radicals, alkoxy radicals, alkylamido radicals, fluoro and fluorohydrocarbyl radicals and the like such as those useful as $X_3$ and $X_4$. The substituent may be ortho, meta or para, relative to the carbon atoms bonded to the boron atom. When either or both $X_3$ and $X_4$ are a hydrocarbyl radical, each may be the same or a different aromatic or substituted-aromatic radical as are Ar and $Ar_2$, or the same may be a straight or branched alkyl, alkenyl or alkynyl radical having from 1 to about 20 carbon atoms, a cyclic hydrocarbon radical having from about 5 to about 8 carbon atoms or an alkyl-substituted cyclic hydrocarbon radical having from about 6 to about 20 carbon atoms. $X_3$ and $X_4$ may also, independently, be alkoxy or dialkylamido radicals wherein the alkyl portion of said alkoxy and dialkylamido radicals contain from 1 to about 20 carbon atoms, hydrocarbyl radicals and organometalloid radicals having from 1 to about 20 carbon atoms and the like. As indicated above, Ar₁ and Ar may be linked to each other. Similarly, either or both of Ar₁ and Ar₂ could be linked to either $X_3$ or $X_4$. Finally, $X_3$ or $X_4$ may also be linked to each other through a suitable bridging group.

Illustrative, but not limiting, examples of boron compounds which may be used as an activator component in the preparation of the improved catalysts of this invention are trialkyl-substituted ammonium salts such as triethylammonium tetra(phenyl)boron, tripropylammonium tetra(phenyl) boron, tri(n-butyl)ammonium tetra(phenyl)boron, trimethylammonium tetra(p-tolyl)boron, trimethylammonium tetra (o-tolyl)boron, tributylammonium tetra(pentafluorophenyl) boron, tripropylammonium tetra(o,p-dimethylphenyl)boron, tributylammonium tetra(m,m-dimethylphenyl)boron, tributylammonium tetra(p-tri-fluoromethylphenyl)boron, tri(n-butyl)ammonium tetra(o-tolyl)boron and the like; N,N-dialkyl anilinium salts such as N,N-dimethylanilinium tetra (pentafluoro phenyl)boron, N,N-diethylanilinium tetra (phenyl)boron, N,N-2,4,6-pentamethylanilinium tetra (phenyl)boron and the like; dialkyl ammonium salts such as di(i-propyl)ammonium tetra(pentafluorophenyl)boron, dicyclohexylammonium tetra(phenyl)boron and the like; and triaryl phosphonium salts such as triphenylphosphonium tetra(phenyl)boron, tri(methylphenyl)phosphonium tetra (phenyl)boron, tri(dimethylphenyl)phosphonium tetra(phenyl)boron and the like.

Similar lists of suitable compounds containing other metals and metalloids which are useful as activator components may be made, but such lists are not deemed necessary to a complete disclosure. In this regard, it should be noted that the foregoing list is not intended to be exhaustive and that other useful boron compounds as well as useful compounds containing other metals or metalloids would be readily apparent to those skilled in the art from the foregoing general equations.

Activator components based on anions which contain a plurality of boron atoms may be represented by the following general formulae:

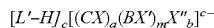
                                                                                6.

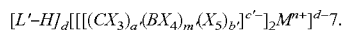
                                                                                7.

wherein [L'–H] is either H⁺, ammonium or a substituted ammonium cation having up to 3 hydrogen atoms replaced with a hydrocarbyl radical containing from 1 to about 20 carbon atoms or a substituted-hydrocarbyl radical, wherein one or more of the hydrogen atoms is replaced by a halogen atom, containing from 1 to about 20 carbon atoms, phosphonium radicals, substituted-phosphonium radicals having up to 3 hydrogen atoms replaced with a hydrocarbyl radical containing from 1 to about 20 carbon atoms or a substituted-hydrocarbyl radical, wherein 1 or more of the hydrogen atoms is replaced by a halogen atom, containing from 1 to about 20 carbon atoms and the like; C is carbon; B" is boron each of X, X', X", $X_3$ $X_4$ and $X_5$ are radicals selected, independently, from the group consisting of hydride radicals, halide radicals, hydrocarbyl radicals containing from 1 to about 20 carbon atoms, substituted-hydrocarbyl radicals, wherein one or more of the hydrogen atoms is replaced by a halogen atom, containing from 1 to 20 carbon atoms, organometalloid radicals wherein each hydrocarbyl substitution in the organo portion contains from 1 to about 20 carbon atoms and said metal is selected from Group IV-A of the Periodic Table of the Elements and the like; M is a transition metal; "a" and "b" are integers≧0; "c" is an integer>1; a+b+c=an even-numbered integer from 2 to about 8; and "m" is an integer ranging from 5 to about 22; "a'" and "b'" are the same or a different integer≧0; "c'" is an integer≧2; a'+b'+c'=an even-numbered integer from 4 to about 8; "m'" is an integer from 6 to about 12; "n" is an integer such that 2c'–n=d; and "d" is an integer greater than or equal to 1.

Illustrative, but not limiting, examples of second components which can be used in preparing catalyst systems utilized in the process of this invention wherein the anion of the second component contains a plurality of metalloid atoms (as in formulae 5 and 6) are ammonium salts such as ammonium 1-carbadodecaborate (using 1-carbadodecaborate as an illustrative, but not limiting, counterion for the ammonium cations listed below): monohydrocarbyl-substituted ammonium salts such as methylammonium 1-carbadodecaborate, ethylammonium 1-carbadodecaborate, propylammonium 1-carbadodecaborate, isopropylammonium 1-carbadodecaborate, (n-butyl)ammonium 1-carbadodecaborate, anilinium 1-carbadodecaborate, and (p-tolyl)ammonium 1-carbadodecaborate and the like; dihydrocarbyl-substituted ammonium salts such as dimethylammonium 1-carbadodecaborate, diethylammonium 1-carbadodecaborate, dipropylammonium 1-carbadodecaborate, diisopropylammonium 1-carbadodecaborate, di(n-butyl) ammonium 1-carbadodecaborate, diphenylammonium 1-carbadodecaborate, di(p-tolyl)ammonium 1-carbadodecaborate and the like; trihydrocarbyl-substituted ammonium salts such as trimethylammonium 1-carbadodecaborate, triethylammonium 1-carbadodecaborate, tripropyl-ammonium 1-carbadodecaborate, tri(n-butyl) ammonium 1-carbadodecaborate, triphenylammonium 1-carbadodecaborate, tri(p-tolyl)ammonium 1-carbadodecaborate, N,N-dimethylanilinium 1-carbadodecaborate, N,N-diethylanilinium 1-carbadodecaborate and the like.

Illustrative, but not limiting examples of second compounds corresponding to Formula 5 [using tri(n-butyl)ammonium as an illustrative, but not limiting, counterion for the anions listed below] are salts of anions such as bis[tri (n-butyl)ammonium] nonaborate, bis[tri(n-butyl)ammonium]decaborate, bis[tri(n-butyl) ammonium]undecaborate, bis[tri(n-butyl)ammonium] dodecaborate, bis[tri(n-butyl) ammoniumldecachlorodecaborate, tri(n-butyl)ammonium dodecachlorododecaborate, tri(n-butyl)ammonium 1-carbadecaborate, tri(n-butyl) ammonium 1-carbaundecaborate, tri (n-butyl)ammonium 1-carbadodecaborate, tri(n-butyl)ammonium 1-trimethylsilyl-1-carbadecaborate, tri(n-butyl) ammonium dibromo-1-carbadodecaborate and the like; borane and carborane complexes and salts of borane and carborane anions such as decaborane(14), 7,8-dicarbaundecaborane(13), 2,7-dicarbaundecaborane(13), undecahydrido-7,8-dimethyl-7,8-dicarbaundecaborane, dodecahydrido-11-methyl-2,7-di-carbaundecaborane, tri(n-butyl) ammonium undecaborate(14), tri(n-butyl)ammonium 6-carbadecaborate(12), tri(n-butyl)ammonium 7-carbaundecaborate(13), tri(n-butyl)ammonium 7,8-dicarbaundecaborate (12), tri(n-butyl)ammonium 2,9-dicarbaundecaborate(12), tri(n-butyl)ammonium dodecahydrido-8-methyl-7,9-dicarbaundecaborate, tri(n-butyl)ammonium undecahydrido-8-ethyl-7,9-dicarbaundecaborate, tri(n-butyl)ammonium undecahydrido-8-butyl-7,9-dicarbaundecaborate, tri(n-butyl)ammonium undecahydrido-8-allyl-7,9-dicarbaundecaborate, tri(n-butyl)ammonium undecahydrido-9-trimethylsilyl-7,8-dicarbaundecaborate, tri(n-butyl)ammonium undecahydrido-4,6-dibromo-7-carbaundecaborate and the like; boranes and carboranes and salts of boranes and carboranes such as 4-carbanonaborane(14), 1,3-dicarbanonaborane(13), 6,9-dicarbadecaborane(14), dodecahydrido-1- phenyl-1,3-dicarbanonaborane, dodecahydrido-1-methyl-1,3-dicarbanonaborane, undecahydrido-1,3-dimethyl-1,3-dicarbanonaborane and the like.

Illustrative, but not limiting, examples of second compounds corresponding to Formula 7 [using tri(n-butyl)ammonium as an illustrative, but not limiting, counterion for the anions listed below] are salts of metallacarborane and metallaborane anions such as tri(n-butyl)ammonium bis(nonahydrido-1,3-dicarbaunaborato) cobaltate(III), tri(n-butyl)ammonium bis(undeca-hydrido-7,8-dicarbaundecaboratoferrate(III), tri(n-butyl) ammonium bis(undecahydrido-7,8-dicarbaundecaborato)cobaltate(III), tri(n-butyl) ammonium bis(undecahydrido-7,8-dicarbaunaborato) nikelate(III), tri(n-butyl)ammonium bis(nonahydrido-7,8-dimethyll-7,8-dicarbaundecaborato)ferrate(III), tri(n-butyl)ammonium bis(nonahydrido-7,8-dimethyll-7,8-dicarbaundecaborato)thromate(III), tri(n-butyl)ammonium bis(tribromooctahydrido-7,8-dicarbaundecaborato)cobaltate (III), tri(n-butyl)ammonium bis(dodecahydridodicarbadodecaborato) cobaltate(III), tris[tri (n-butyl)ammonium] bis (undecahydrido-7-carbaundecaborato)chromate(III), bis[tri(n-butyl) ammonium] bis(undecahydrido-7-carbaundecaborato)manganate(IV), bis[tri(N-butyl)ammonium] bis(undecahydrido-7-carbaundecaborato) cobaltate(III), bis[tri (n-butyl)ammonium] bis(undecahydrido-7-carbaundecaborato) nickelate (IV) and the like. A similar list of representative phosphonium compounds can be recited as illustrative second compounds, but for the sake of brevity, it is simply noted that the phosphonium and substituted-phosphonium salts corresponding to the listed ammonium and substituted-ammonium salts could be used as second compounds in the present invention.

Process of Catalyst Preparation

The catalyst systems employed in the method of the invention comprise a complex formed upon admixture of the Group IV-B transition metal component with the activator component. The catalyst system may be prepared by addition of the requisite Group IV-B transition metal and activator components to an inert solvent in which olefin polymerization can be carried out by a solution polymerization procedure.

The catalyst system may be conveniently prepared by placing the selected Group IV-B transition metal component and the selected activator component, in any order of addition, in an alkane or aromatic hydrocarbon solvent—preferably toluene. The catalyst system may be separately prepared, in concentrated form, and added to the polymerization diluent in a reactor. Or, if desired, the components of the catalyst system may be prepared as separate solutions and added to the polymerization diluent in a reactor, in appropriate ratios, as is suitable for a continuous liquid polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutene, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, butene, 1-hexene and the like.

In accordance with this invention optimum results are generally obtained wherein the Group IV-B transition metal compound is present in the polymerization diluent in concentration of from about 0.01 to about 1.0 millimolesiliter of diluent and the activator component is present in an amount to provide a molar ratio of the transition metal to activator component preferably from about 1:1 to about 200:1. Sufficient solvent should be employed so as to provide adequate heat transfer away from the catalyst components during reaction and to permit good mixing.

The catalyst system ingredients—that is, the Group IV-B transition metal and activator components, and polymerization diluent can be added to the reaction vessel rapidly or slowly. The temperature maintained during the contact of the catalyst components can vary widely, such as, for example, from $-100°$ to $300°$ C. Greater or lesser temperatures can also be employed. Preferably, during formation of the catalyst system, the reaction is maintained within a temperature of from about $25°$ to $100°$ C., most preferably about $25°$ C.

At all times, the individual catalyst system components, as well as the catalyst system once formed, are protected from oxygen and moisture. Therefore, the reactions are performed in an oxygen and moisture free atmosphere and, where the catalyst system is recovered separately, it is recovered in an oxygen and moisture-free atmosphere. Preferably, therefore, the reactions are performed in the presence of an inert dry gas such as, for example, helium or nitrogen.

The Catalyst System: Characterization and Properties of the Active Site

The reaction of the two catalyst components can be viewed as a simple acid-base reaction where the $Q^-$-ligand bound to the transition metal center of $(CN)MQ_2$ (where (CN)=the Cp and J-ligands) reacts with the acidic cation of the second component, $[L'H^+][A]^-$ (where $A^-$ is the non-coordinating anion), to give the ionic catalyst $[(CN)MQ]^+$ [A]' and neutral biproducts Q–H and L'. The overall catalytic performance of the catalyst depends on the choice of metal, the specific (CN)-ligand set, the structure and stability of $A^-$, and the coordinating ability of the Lewis base L'. For conventional applications where a high productivity homopolymerization or random copolymerization catalyst is desired, the Q-ligand of the transition metal component is chosen so that: 1) the metal complex is easy to prepare and is low cost, 2) $(CN)MQ_2$ is sufficiently basic to deprotonate the acidic cation of the activator component, and 3) Q–H is an unreactive biproduct such as an alkane so that the activation reaction is irreversible. For a particular (CN)M-system the L' and $A^-$ portions of the activator component "tune" the stability and overall performance of the catalyst system. The ability of L' and $A^-$ to modify the behavior of a catalyst site increases the versatility of the polymerization system which is an important advantage over conventional methods of activation (e.g. methylalumoxane, and other aluminum alkyl cocatalysts).

In general, and while most transition metal components identified above may be combined with most activator components identified above to produce an active olefin polymerization catalyst, it is important for continuity of the polymerization operations that either the metal cation initially formed from the first component or a decomposition product thereof be a relatively stable catalyst. It is also important that the anion of the activator compound be stable to hydrolysis when an ammonium salt is used. Further, it is important that the acidity of the activator component be sufficient, relative to the metal component, to facilitate the needed proton transfer. Activator compounds containing aryl-ammonium salts such as N,N-dimethylanilium are more acidic than trialkylammonium salts and therefore are useful with a wider variety of transition metal components. The basicity of the metal complex must also be sufficient to facilitate the needed proton transfer. In general, transition metal compounds which can be hydrolyzed by aqueous solutions can be considered suitable as metallocene components to form the catalysts described herein.

With respect to the combination of the transition metal component with the activator component to form a catalyst of this invention, it should be noted that the two compounds combined for preparation of the active catalyst must be selected so as to avoid transfer of a fragment of the anion to the metal cation, thereby forming a catalytically inactive species. This could be done by steric hindrance, resulting from substitutions on the Cp- and/or J-ligands of the first component, as well as substitutions on the non-coordinating anion.

As the amount and size of the substitutions on the transition metal components are reduced, more effective catalysts are obtained with activator compounds containing non-coordinating anions which are larger in size and more resistant to degradation. In the case where the non-coordinating anion is an anionic coordination complex, such as a tetraphenylboron derivative, substitutions on the phenyl rings can be used to prevent the transfer of a proton or an entire phenyl group from the anion to the metal. This can be accomplished by alkyl substitution in the ortho positions of the phenyl groups, or, more preferably, by perfluoro-substitutions on the anion. Thus, anionic coordination complexes containing perfluorphenyl-, trifluoromethylphenyl-, or bis-trifluormethylphenyl rings are preferred for this subgenus of activator components. When the non-coordinating anion contains a plurality of boron atoms as described in general formulae 6 and 7, more effective catalysts are obtained with activator compounds containing larger anions, such as those encompassed by Equation 7 and those having larger-m values in Equation 6. In these cases it is further preferable when using second compounds which are encompassed by Equation 6, that a+b+c=2. Second compounds in which a+b+c=even-numbered integers of 4 or more have acidic B–H–H–B moieties which can react further with the metal cation formed, leading to catalytically inactive compounds.

Several new compositions of matter have been identified using high field NMR spectroscopy. The reaction between $Me_2Si(Me_4C_5)(N\text{-}t\text{-}Bu)ZrMe_2$ and $[DMAH][B(pfp)_4]$ (where DMAH=$PhMe_2NH^+$ and pfp $C_6F_5$) in $d_8$-toluene produces a two phase system. The top layer is largely $d_8$toluene with only a very small amount of DMA (DMA— $PhNMe_2$) present. The lower layer Got contains the ionic catalyst and $d_8$-toluene. The high field $^{13}C$ NMR spectrum of the lower layer shows the action proceeds to give the DMA-adduct as shown below in Roman Numeral I.

II

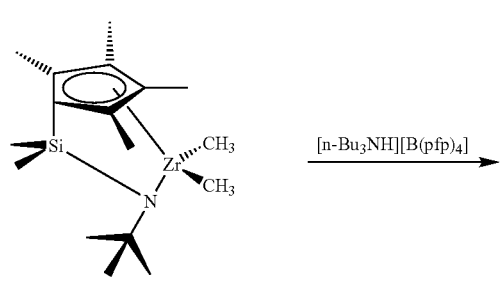

[n-Bu$_3$NH][B(pfp)$_4$]

-continued

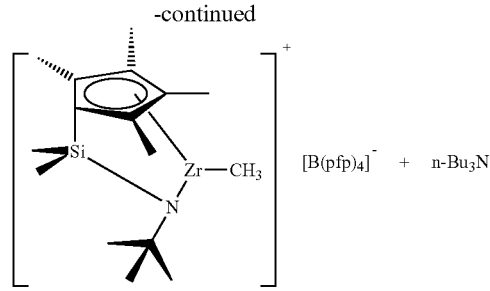

[B(pfp)$_4$]$^-$ + n-Bu$_3$N

The NMR data clearly demonstrates that the amine is indeed coordinated to the zirconium atom, but that it is fluxional and probably has two orientations of coordination, most likely in the form of rotational isomers. The ionic catalysts species can be crystallized out at –40° C. giving a pale blue power. The solid state NMR spectrum of this material revealed amine coordination to the zirconium atom with more than one orientation. Addition of $d_8$-thf (thf=tetrahydrofuran) to the catalyst solution or solid produces the $d_8$-thf adduct, $Me_2Si(Me_4C5)(N\text{-}t\text{-}Bu)ZrMe(d_8\text{-}thf)_x][B(pfp)_4]$ and free DMA. This was expected since $d_8$-thf is a much stronger base than DMA.

Ion-exchange activators with different basicities have also been investigated. An amine which is a stronger base than DMA, such as DMT ($Me_2N\text{-}p\text{-}Me\text{-}Ph$) provides complete coordination to the zirconium atom with no fluxionality. This catalyst was produced from the reaction of $[DMTH][B(pfp)_4]$ with $Me_2Si(Me_4C_5)(N\text{-}t\text{-}Bu)ZrMe_2$. Very little, if any, free DMT was observed in the $^{13}C$ NMR spectrum of the catalyst solution. The use of $[Bu_3NH][B(pfp)_4]$ as the activator provided a more interesting result. It appears that when $[n\text{-}Bu_3NH][B(pfp)_4]$ is reacted with $Me_2Si(Me_4c_5)(N\text{-}t\text{-}Bu)ZrMe_2$, the amine does not coordinate to the zirconium atom as illustrated in Roman Numeral II above.

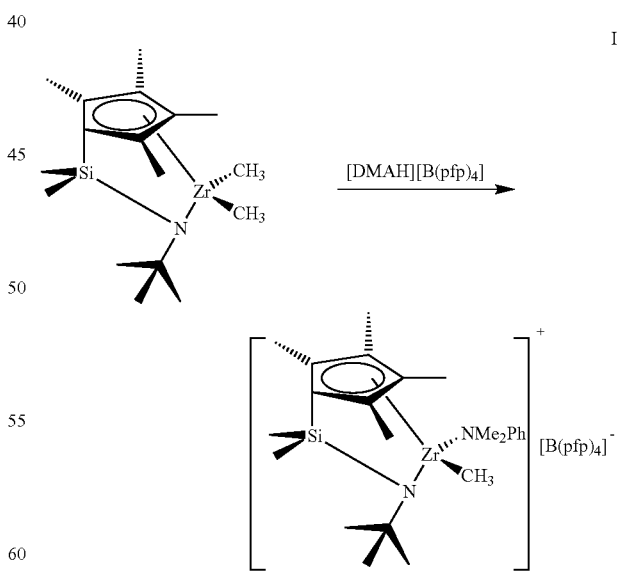

The fact that the amine is not coordinated to the metal is evidenced by the fact that the chemical shift of the amine signals are unchanged from free-amine. From a purely electronic point of view one would predict that Bu$_3$N would be a better ligand for the cationic metal center than DMA.

The reverse is the case in this system indicating that steric forces dominate the coordination chemistry. The observation of two Cp-methyl signals and one $Me_2Si$-signal demonstrates that the cation is a symmetric three coordinate cation and that anion and the amine ligand to not coordination strongly with the metal to destroy the plane of symmetry through the metal, the Cp-centroid, and the silicon atom.

The reaction of $Me_2Si(Me_4C_5)(N-t-Bu)ZrMe_2$ with $[DMAH][(C_2B_9H_{11})_2Co]$ was also investigated by high field NMR. In this case the amine, DMA, is not coordinated to the metal. The fact that one observes four Cp-methyl signals and two $Me_2Si$ signals in the $^{13}C$ NMR spectrum demonstrates that the metallacarborane is coordinated to the metal center. This is consistent with its high solubility and low activity relative to the $B(pfp)_4$ system.

Polymerization Process

In a preferred embodiment of the process of this invention the catalyst system is utilized in a liquid phase polymerization of an olefin monomer. The liquid phase process comprises the steps of contacting an olefin monomer with the catalyst system in a suitable polymerization diluent and reacting said monomer in the presence of said catalyst system for a time and at a temperature sufficient to produce a polyolefin.

The monomer for such process may comprise ethylene alone, for the production of a homopolyethylene, or ethylene in combination with an α-olefin having 3 to 18 carbon atoms for the production of an ethylene-α-olefin copolymer. Conditions most preferred for the homo- or copolymerization of ethylene are those wherein ethylene is submitted to the reaction zone at pressures of from about 0.019 psi to about 50,000 psi and the reaction temperature is maintained at from about −100° C. to about 300° C., preferably −10° to 220° C. The mole ratio of transition metal component to activator component is preferably from about 1:1 to about 200:1. The reaction time is preferably from about 1 second to about 1 hour.

Without limiting in any way the scope of the invention, one means for carrying out the process of the present invention is as follows: in a stirred-tank reactor liquid 1-butene monomer is introduced. The catalyst system is introduced via nozzles in either the vapor or liquid phase. Feed ethylene gas is introduced either into the vapor phase of the reactor, or sparged into the liquid phase as is well known in the art. The reactor contains a liquid phase composed substantially of liquid 1-butene together with dissolved ethylene gas, and a vapor phase containing vapors of all monomers. The reactor temperature and pressure may be controlled via reflux of vaporizing a-olefin monomer (autorefrigeration), as well as by cooling coils, jackets, etc. The polymerization rate is controlled by the rate of catalyst addition, or by the concentration of catalyst. The ethylene content of the polymer product is determined by the ratio of ethylene to 1-butene in the reactor, which is controlled by manipulating the relative feed rates of these components to the reactor.

EXAMPLES

In the examples which illustrate the practice of the invention the analytical techniques described below were employed for the analysis of the resulting polyolefin products. Molecular weight determinations for polyolefin products were made by Gel Permeation Chromatography (GPC) according to the following technique. Molecular weights and molecular weight distributions were measured using a Waters 150 gel permeation chromatograph equipped with a differential refractive index (DRI) detector and a Chromatix KMX-6 on-line light scattering photometer. The system was used at 135° C. with 1,2,4-trichlorobenzene as the mobile phase. Shodex (Showa Denko America, Inc.) polystyrene gel columns 802, 803, 804 and 805 were used. This technique is discussed in "Liquid Chromatography of Polymers and Related Materials III", J. Cazes, Editor, Marcel Dekker, 1981, p. 207 which is incorporated herein by reference. No corrections for column spreading were employed; however, data on generally accepted standards, e.g. National Bureau of Standards Polyethylene 1484 and anionically produced hydrogenated polyisoprenes (an alternating ethylene-propylene copolymer) demonstrated that such corrections on Mw/Mn (MID) were less than 0.05 units. Mw/Mn was calculated from elution time. The numberical analyses were performed using the commercially available Beckman/CIS customized LALLS software in conjunction with the standard Gel Permeation package, run on a HP 1000 computer.

The following examples are intended to illustrate specific embodiments of the invention and are not intended to limit the scope of the invention.

All procedures were performed under an inert atmosphere of helium or nitrogen. Solvent choices are often optional, for example, in most cases either pentane or 30-60 petroleum ether can be interchanged. The choice between tetrahydrofuran (thf) and diethyl ether is more restricted, but in several reactions, either could be used. The lithiated amides were prepared from the corresponding amines and either n-BuLi or MeLi. Published methods for preparing $LiHC_5Me_4$ include C. M. Fendrick et al. *Organometallics*, 3,819 (1984) and F. H. Kohler and K. H. Doll, Z. *Natureorsch*, 376, 144 (1982). Other lithiated substituted cyclopentadienyl compounds are typically prepared from the corresponding cyclopentadienyl and BuLi or MeLi, or by reaction of MeLi with the proper fulvene. $ZrCl_4$ and $HfCl_4$ were purchased from either Aldrich Chemical Company or Cerac. Amines, silane and lithium reagents were purchased from Aldrich Chemical Company or Petrarch Systems. Activator components were prepared by known literature methods.

EXAMPLES

Synthesis of Mono-Cyclopentadienyl Complexes

1. $Me_2Si(C_5Me_4)(N-t-Bu)ZrMe_2$

Part 1. $Me_4HC_5Li$ (10.0 g, 0.078 mol) was slowly added to a $Me_2SiCl_2$ (11.5 ml, 0.095 mol, in 225 ml of tetrahydrofuran (thf) solution). The solution was stirred for 1 hour to assure complete reaction. The thf solvent was then removed via a vacuum to a cold trap held at −196° C. Pentane was added to precipitates the LiCl. The mixture was filtered through Celite. The solvent was removed from the filtrate. $Me_4HC_5SiMe_2Cl$ (15.34 g, 0.071 mol) was recovered as a pale yellow liquid.

Part 2. $Me_4HC_5SiMe_2Cl$ (10.0 g, 0.047 mol) was slowly added to a suspension of LiHN-t-Bu (3.68 g, 0.047 mol, ~100 ml thf). The mixture was stirred overnight. The thf was then removed via a vacuum to a cold trap held at −196° C. Petroleum ether (~100 ml) was added to precipitate the LiCl. The mixture was filtered through Celite. The solvent was removed from the filtrate. $Me_2Si(Me_4HC_5)(HN-t-Bu)$ (11.14 g, 0.044 mol) was isolated as a pale yellow liquid.

Part 3. $Me_2Si(Me_4HC_5)(HN-t-Bu)$ (11.14 g, 0.044 mol) was diluted with ~100 ml $Et_2O$. MeLi (1.4 M, 64 ml, 0.090 mol) was slowly added. The mixture was allowed to stir for ½ hour after the final addition of MeLi. The ether was reduced in volume prior to filtering off the product. The product, [Me$_2$Si(Me$_4$C$_5$)(N-t-Bu)]Li$_2$, was washed with several small portions of ether, then vacuum dried.

Part 4. [Me$_2$Si(Me$_4$C$_5$)(N-t-Bu)]Li$_2$ (3.0 g, 0.011 mol) was suspended in ~150 ml Et20. ZrCl$_4$ (2.65 g, 0.011 mol) was slowly added and the resulting mixture was allowed to stir overnight. The ether was removed via a vacuum to a cold trap held at −196° C. Pentane was added to precipitated the LiCl. The mixture was filtered through Celite twice. The pentane was significantly reduced in volume and the pale yellow solid was filtered off and washed with solvent. Me$_2$Si(Me$_4$C$_5$)(N-t-Bu)ZrCl$_2$ (1.07 g, 0.0026 mole) was recovered. Additional Me$_2$Si(Me$_4$C$_5$)(N-t-Bu)ZrCl$_2$ was recovered from the filtrate by repeating the recrystallization procedure. Total yield, 1.94 g, 0.0047 mol).

Part 5. Me$_2$Si(C$_5$Me$_4$)(N-t-Bu)ZrMe$_2$ was prepared by adding a stoichiometric amount of MeLi (1.4 M in ether) to Me$_2$Si(C$_5$Me$_4$)(N-t-Bu)ZrCl$_2$ suspended in ether. The white solid was isolated in an 83X yield.

2. MePhSi(C$_5$Me$_4$)(N-t-Bu)HfMe$_2$

Part 1. MePhSiCl$_2$ (14.9 g, 0.078 mol) was diluted with ~250 ml of thf. Me$_4$C$_5$HLi (10.0 g, 0.078 mol) was slowly added as a solid. The reaction solution was allowed to stir overnight. The solvent was removed via a vacuum to a cold trap held at −196° C. Petroleum ether was added to precipitate the LiCl. The mixture was filtered through Celite, and the pentane was removed from the filtrate. MePhSi(Me$_4$C$_5$H)Cl (20.8 g, 0.075 mol) was isolated as a yellow viscous liquid.

Part 2. LiHN-t-Bu (4.28 g, 0.054 mol) was dissolved in ~100 ml of thf. MePhSi(Me$_4$C$_5$H)Cl (15.0 g, 0.054 mol) was added drop wise. The yellow solution was allowed to stir overnight. The solvent was removed via vacuum. Petroleum ether was added to precipitate the LiCl. The mixture was filtered through Celite, and the filtrate was evaporated down. MePhSi(Me$_4$C$_5$H)(NH-t-Bu) (16.6 g, 0.053 mol) was recovered as an extremely viscous liquid.

Part 3. MePhSi(Me$_4$C$_5$H)(NH-t-Bu) (16.6 g, 0.053 mol) was diluted with ~100 ml of ether. MeLi (76 ml, 0.106 mol, 1.4 M) was slowly added and the reaction mixture was allowed to stir for ~3 hours. The ether was reduced in volume, and the lithium salt was filtered off and washed with pentane producing 20.0 g of a pale yellow solid formulated as Li$_2$[MePhSi(Me$_4$C$_5$)(N-t-Bu)]•¾Et$_2$0.

Part 4. Li$_2$[MePhSi(Me$_4$C$_5$)(N-t-Bu)]•¾Et$_2$O (5.00 g, 0.0131 mol) was suspended in ~100 ml of Et$_2$O. HfCl$_4$ (4.20 g, 0.0131 mol) was slowly added and the reaction mixture was allowed to stir overnight. The solvent was removed via vacuum and petroleum ether was added to precipitate the LiCl. The mixture was filtered through Celite. The filtrate was evaporated to near dryness and filtered. The off white solid was washed with petroleum ether. MePhSi(Me$_4$C$_5$)(N-t-Bu)HfCl$_2$ was recovered (3.54 g, 0.0058 mole).

Part 5. MePhSi(Me$_4$C$_5$)(N-t-Bu)HfMe$_2$ was prepared by adding a stoichiometric amount of MeLi (1.4 M in ether) to MePhSi(Me$_4$C$_5$)(N-t-Bu)HfCl$_2$ suspended in ether. The white solid could be isolated in near quantitative yield.

POLYMERIZATIONS

Example 1

A catalyst solution prepared from 19.7 mg of Me$_2$Si(Me$_4$C$_5$)(N-t-Bu)ZrMe$_2$ and 6 mg of [DMAH] [B(pfp)$_4$] in 20 mls of toluene was added to a 1 liter stainless-steel autoclave containing 400 mls of hexane. The reactor temperature was maintained at 40° C. and stirred vigorously while ethylene was added at 90 psi. After 30 minutes the reaction was stopped giving 30 grams of HDPE after work-up. The GPC analysis showed a bimodal distribution with modes centered at 900,000 and 2,000.

Example 2

A catalyst solution prepared from 28.6 mg of Me$_2$Si(Me$_4$C$_5$)(N-t-Bu)ZrMe$_2$ and 9 mg of [DMAH] [B(pfp)$_4$] in 20 mls of toluene was added to a 1 liter stainless-steel autoclave containing 400 mls of hexane. The reactor temperature was set at 50° C. and was stirred vigorously while 100 mls of butene and 60 psi of ethylene were added. Following the addition of butene and ethylene, an instantanious increase in temperature to 90° C. was observed. After 30 minutes the reaction was stopped, yielding 130 grams of a waxy ethylene-butene copolymer. GPC analysis showed a bimodal distribution with modes centered at 27,000 and 2,000 in approximately equal ratios. IR spectroscopy showed the presence of butene in the copolymer.

Example 3

A catalyst solution prepared from 40 mg of MePhSi(C$_5$Me$_4$)(N-t-Bu)HfMe$_2$ and 11 mg of [DMAH][]B(pfp)$_4$] in 20 mls of toluene was added to a 1 liter autoclave containing 400 mls of hexane. The reactor temperature was set at 40° C., stirred vigorously and pressurized with ethylene (90 psi) for 15 minutes. The reactor temperature increased from 40 to 97° C. during the polymerization. The reactor was stopped and 98 grams of polyethylene was isolated having a Mw=47.7 K and a MWD=3.0.

Example 4

A catalyst solution prepared from 50 mg of Me$_2$Si(C$_5$Me$_4$)(N-t-Bu)ZrMe$_2$ and 68 mg of [DMAH][(C$_2$B$_9$H$_{11}$)$_2$Co] in 20 mls of toluene was added to a 1 liter autoclave containing 400 mls of hexane. The reactor temperature was set at 60° C., stirred vigorously and pressurized with ethylene (120 psi) for 60 minutes. The reactor was stopped and 0.44 grams of polyethylene was isolated having a Mw=538 K and a MWD=1.90.

The invention claimed is:

1. A catalyst system for the production of polyolefins comprising:

(A) a Group IV B transition metal component represented by one of the two general formulae

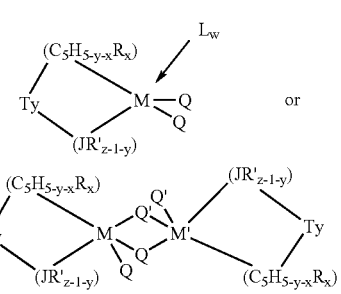

wherein M is Zr, Hf or Ti and is in its highest formal oxidation state (+4, d$^0$ complex);

$(C_5H_{5-y-x}R_x)$ is a cyclopentadienyl ring which is substituted with from zero to five radical R groups, "x" is 0, 1, 2, 3, 4 or 5 denoting the degree of substitution, and each substituent R group is, independently, a radical selected from the group consisting of $C_1$–$C_{20}$ hydrocarbyl radicals, substituted $C_1$–$C_{20}$ hydrocarbyl radicals wherein one or more hydrogen atoms are replaced by a halogen atom, $C_1$–$C_{20}$ hydrocarbyl-substituted metalloid radicals wherein the metalloid is selected from the group consisting of germanium and silicon, and halogen radicals; or $(C_5H_{5-y-x}R_x)$ is a cyclopentadienyl ring in which two adjacent R groups are joined forming a $C_4$–$C_{20}$ ring to give a saturated or unsaturated polycyclic cyclopentadienyl ligand;

$(JR'_{z-l-y})$ is a heteroatom ligand in which J is an element with a coordination number of three from Group V-A or an element with a coordination number of two from Group VI-A of the Periodic Table of Elements, each R' is, independently, a radical selected from the group consisting of $C_1$–$C_{20}$ hydrocarbyl radicals and substituted $C_1$–$C_{20}$ hydrocarbyl radicals, wherein one or more hydrogen atoms is replaced by a halogen atom, and "z" is the coordination number of the element J;

each Q is independently, hydride, $C_1$–$C_{20}$ hydrocarbyl radicals, substituted hydrocarbyl radicals wherein one or more hydrogen atoms is replaced by an electron withdrawing group, or $C_1$–$C_{20}$ hydrocarbyl-substituted metalloid radicals wherein the metalloid is selected from the group consisting of germanium and silicon, provided that Q is not a substituted or unsubstituted cyclopentadienyl ring, or both Q together may be an alkylidene, olefin, acetylene or a cyclometallated hydrocarbyl;

"y" is 0 or 1; when "y" is 1, T is a covalent bridging group containing a Group IV-A or V-A element;

L is a neutral Lewis base; and "w" is a number from 0 to 3; wherein M' has the same meaning as M and Q' has the same meaning as Q; and (B) an activator compound comprising (1) a cation; and (2) a compatible noncoordinating anion.

2. A catalyst system comprising;

(A) a Group IV-B transition metal component represented by the formula

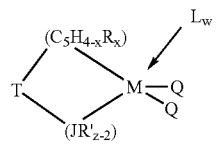

wherein M is Zr, Hf or Ti;

$(C_5H_{4-x}R_x)$ is a cyclopentadienyl ring which is substituted with from zero to four radical R groups, "x" is 0, 1, 2, 3, or 4 denoting the degree of substitution, and each substituent R group is, independently, a radical selected from the group consisting of $C_1$–$C_{20}$ hydrocarbyl radicals and substituted $C_1$–$C_{20}$ hydrocarbyl radicals, wherein one or more hydrogen atoms are replaced by a halogen atom, $C_1$–$C_{20}$ hydrocarbyl-substituted metalloid radicals wherein the metalloid is selected from the group consisting of germanium and silicon, and halogen radicals; or $(C_5H_{4-x}R_x)$ is a cyclopentadienyl ring in which two adjacent R groups are joined forming a $C_4$–$C_{20}$ ring to give a saturated or unsaturated polycyclic cyclopentadienyl ligand;

$(JR'_{z-2})$ is a heteroatom ligand in which J is an element with a coordination number of three from Group V-A or an element with a coordination number of two from Group VI-A of the Periodic Table of Elements, each R' is, independently, a radical selected from the group consisting of $C_1$–$C_{20}$ hydrocarbyl radicals and substituted $C_1$–$C_{20}$ hydrocarbyl radicals, wherein one or more hydrogen atoms is replaced by a halogen atom, and "z" is the coordination number of the element J;

each Q is independently hydride, $C_1$–$C_{20}$ hydrocarbyl radicals, substituted hydrocarbyl radicals wherein one or more hydrogen atoms is replaced by an electron withdrawing group, or $C_1$–$C_{20}$ hydrocarbyl-substituted metalloid radicals wherein the metalloid is selected from the group consisting of silicon and germanium, provided that Q is not a substituted or unsubstituted cyclopentadienyl ring, or both Q together may be an alkylidene, olefin, acetylene or a cyclometallated hydrocarbyl;

T is a linear, branched or cyclic alkylene group having from 1 to 6 carbon atoms, a silylene group having from 1 to 2 silicon atoms, or a group containing a Group IV-A or V-A element;

L is a neutral Lewis base; and "w" is a number from 0 to 3; and (B) an activator component comprising (1) a cation; and (2) a compatible noncoordinating anion.

3. The catalyst system of claim 2 wherein said cation of said activator component is a Bronsted acid.

4. The catalyst system of claim 2 wherein said cation of said activator compound is such that it will irreversibly react with at least one Q ligand.

5. The catalyst system of claim 2 wherein said anion of said activator component is a single anionic coordination complex having a plurality of lipophilic radicals covalently coordinated to and shielding a central charge bearing metal or metalloid atom.

6. The catalyst system of claim 1 or 2, wherein said activator compound is represented by the formula:

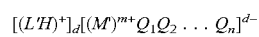

$$[(L'H)^+]_d[(M')^{m+}Q_1Q_2\ldots Q_n]^{d-}$$

wherein:

L' is a neutral Lewis base; H is a hydrogen atom; [L'–H] is a Bronsted acid; M' is a metal or metalloid selected from the group consisting of Groups V-B, VI-B, VII-B, VIII, I-B, II-B, III-A, IV-A, and V-A of the Periodic Table of the Elements; $Q_1$ to $Q_n$ are independently, hydride, dialkylamido, alkoxide, aryloxide, hydrocarbyl, and substituted-hydrocarbyl and any one, but not more than one of $Q_1$ to $Q_{11}$ may be halide radical; "m" is an integer from 1 to 7; "n" is an integer from 2 to 8; and n–m="D".

7. The catalyst system of claim 6, wherein said activator compound is represented by the formula:

$$[L'-H]^+p[BAr_1Ar_2X_3X_4]$$

wherein:

B is boron in a valence state of three;

$Ar_1$ and $Ar_2$ are the same or different aromatic or substituted-aromatic hydrocarbon radicals, which radicals may be linked to each other through a stable bridging group; and $X_3$ and $X_4$, are independently, a hydride, halide, hydrocarbyl, or a substitated-hydrocarbyl.

8. The catalyst of claim 7, wherein said activator compound is represented by the formula;

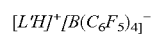

$$[L'H]^+[B(C_6F_5)_4]^-$$

9. The catalyst system of claim 7 wherein the heteroatom ligand group J element is nitrogen.

10. The catalyst system of claim 7 wherein M is zirconium.

11. The catalyst system of claim 7 wherein "x" is 4.

12. The catalyst system of claim 7 wherein M is hafnium.

13. The catalyst system of claim 2 where T is an alkyl or aryl substituted silylene group having from 1 to 2 silicon atoms in the bridge, or a linear, branched or cyclic alkylene.

14. The catalyst system of claim 1 or 2 wherein said activator compound is represented by the formulae:

$$[L'-H]_c[(CX)_a(BX')_mX''_b]^{c-or}$$

$$[L'-H]_d[[[(CX_3)_a(BX_4)_m(X_5)_b]^{c'-}]_2M^{n+}]^{d-}$$

wherein [L'-H] is a cation selected from the group consisting of a H$^+$; an ammonium; a substituted ammonium wherein the substituted ammonium cation has up to three hydrogen atoms replaced with a radical selected from a group consisting of a hydrocarbyl radical containing from 1 to about 20 carbon atoms and a substituted-hydrocarbyl radical containing from 1 to 20 carbon atoms wherein one or more of the hydrogen atoms is replaced by a halogen atom; a phosphonium; and a substituted-phosphonium wherein the substituted phosphonium cation has up to three hydrogen atoms replaced with a radical selected from a group consisting of a hydrocarbyl radical containing from 1 to about 20 carbon atoms and a substituted-hydrocarbyl radical containing from 1 to 20 carbon atoms wherein one or more of the hydrogen atoms is replaced by a halogen atom; C is carbon; B is boron; each of X, X', X", X$_3$ X$_4$ and X$_5$ are radicals selected, independently, from the group consisting of hydride radicals, halide radicals, hydrocarbyl radicals containing from 1 to about 20 carbon atoms, substituted-hydrocarbyl radicals containing from 1 to 20 carbon atoms wherein one or more of the hydrogen atoms is replaced by a halogen atom, organometalloid radicals wherein each hydrocarbyl substitution in the organo portion contains from 1 to about 20 carbon atoms, and said metalloid is selected from the group consisting of silicon; M is a transition metal; "a" and "b" are integers $\geq 0$; "c" is an integer $\geq 1$; a+b+c=an even-numbered integer from 2 to 8; and "m" is an integer ranging from 5 to 22; "a'"and "b'" are the same or a different integer $\geq 0$; "c'" is an integer $\geq 2$; a'+b'+c'=an even-numbered integer from 4 to 8; "m'" is an integer from 6 to 12; "n" is an integer such that 2c'–n=d; and "d" is an integer greater than or equal to 1.

15. The catalyst system of claim 2 wherein J is nitrogen.

16. The catalyst system of claim 2 where M is titanium or zirconium.

17. The catalyst system of claim 2 wherein the Group IV-B transition metal component is represented by the formula

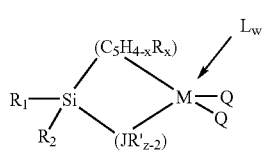

wherein R$_1$ and R$_2$ are, together, a substituted or unsubstituted dialkyl, diaryl or alkylaryl group; R$_1$ and R$_2$ may also be joined forming a ring.

18. The catalyst system of claim 17 wherein J is nitrogen.

19. The catalyst system of claim 18 wherein M is titanium or zirconium.

20. The catalyst system of claim 1 wherein the heteroatom ligand group J element is nitrogen, phosphorous, oxygen or sulfur.

21. The catalyst system of claim 20, wherein "y" is 1 and "T" is a linear, branched or cyclic alkylene group having from 1 to 6 carbon atoms, an alkyl substituted silylene group having from 1 to 2 silicon atoms in place of carbon atoms in the bridge, or a Si$_1$–Si$_2$ alkyl substituted silylene group.

22. The catalyst system of claim 21 wherein the heteroatom ligand group J element is nitrogen.

23. The catalyst system of claim 22 wherein "T" is an alkyl substituted silylene group having from 1 to 2 silicon carbon atoms in the bridge, or a Si$_1$–Si$_2$ alkyl substituted silylene group.

24. The catalyst system of claim 1 wherein said anion of said activator compound is a single anionic coordination complex having a plurality of lipophilic radicals covalently coordinated to and shielding a central charge bearing metal or metalloid atom.

25. The catalyst system of claim 1 wherein said cation of said acitivator compound is such that it will irreversibly react with at least one Q ligand.

26. The catalyst system of claim 1 wherein said cation of said activator compound is a Bronsted acid.

27. The catalyst system of claim 1 wherein said anion of said activator compound is of a size such that said anion is sterically hindered from coordinating to the Group IV-B metal, and said anion is labile such that said anion is capable of being displaced from said Group IV-B metal by an unsaturated hydrocarbon having a Lewis base strength equal to or greater than ethylene.

28. A composition of matter comprising the following general formula:

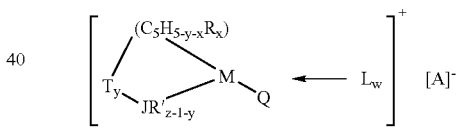

wherein: M is Zr, Hf or Ti and is in its highest formal oxidation state (+4, d$^0$ complex);

(C$_5$H$_{5-y-x}$R$_x$) is a cyclopentadienyl ring which is substituted with from zero to five substituent R groups, "x" is 0, 1, 2, 3, 4 or 5 denoting the degree of substitution, and each substituent group R is, independently, a radical selected from the group consisting of C$_1$–C$_{20}$ hydrocarbyl radicals, and substituted C$_1$–C$_{20}$ hydrocarbyl radicals wherein one or more hydrogen atoms is replaced by a halogen atom, C$_1$–C$_{20}$ hydrocarbyl-substituted metalloid radicals wherein the metalloid is selected from the group consisting of silicon and germanium, and halogen radicals, or (C$_5$H$_{5-y-x}$R$_x$) is a cyclopentadienyl ring in which two adjacent R groups are joined forming a C$_4$–C$_{20}$ ring to give a saturated or unsaturated polycyclic cyclopentadienyl ligand;

(JR'$_{z-1-y}$) is a heteroatom ligand in which J is an element with a coordination number of three from Group V-A or an element with a coordination number of two from Group VI-A of the Periodic Table of Elements, and each R' is, independently, a radical selected from the group consisting of C$_1$–C$_{20}$ hydrocarbyl radicals, and substituted C$_1$–C$_{20}$ hydrocarbyl radicals wherein one or more hydrogen atoms is replaced by a halogen atom, and "z" is the coordination number of the element J;

Q is a hydride, $C_1$–$C_{20}$ hydrocarbyl radical, substituted hydrocarbyl radical wherein one or more hydrogen atoms are replaced by an electron-withdrawing group, or $C_1$–$C_{20}$ hydrocarbyl-substituted metalloid radical wherein the metalloid is selected from the group consisting of germanium and silicon, provided that Q is not a substituted or unsubstituted cyclopentadienyl ring;

"y" is 0 or 1; when "y" is 1, T is a covalent bridging group containing a Group IV A or V A element;

L is a neutral Lewis base; and "w" is a number from 0 to 3,

[A]⁻ is a compatible noncoordinating anion.

29. The composition of matter of claim 28 wherein [A]⁻ is represented by the following general formula

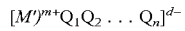

wherein M' is a metal or metalloid selected from the group consisting of Groups V-B, VI-B, VII-B, VIII, I-B, II-B, III-A, IV-A, and V-A of the Periodic Table of the Elements;

$Q_1$ to $Q_n$ are selected, independently, from the groups consisting of hydride radicals, dialkylamido radicals, alkoxide and aryloxide radicals, hydrocarbyl and substituted-hydrocarbyl radicals and any one, but not more than one, of $Q_1$ to $Q_n$ may be a halide radical, the remaining $Q_1$ to $Q_n$ being, independently, selected from the foregoing radicals;

m is an integer from 1 to 7;

n is an integer from 2 to 8; and n−m=d.

30. The composition of matter of claim 29 wherein [A]' is [$B(C_6F_5)_4$]'.

31. The composition of matter of claim 28 wherein [A]' is represented by the following general formula:

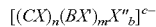

or [[[$(CX_3)_n(BX_4)_m(X_5)_{b'}$]$^{C'}$]$_2M^{m+}$]$^{d-}$

C is carbon; B is boron; each of X, C', X", $X_3X_4$ and $X_5$ are radicals selected, independently, from the group consisting of hydride radicals, halide radicals, hydrocarbyl radicals containing from 1 to about 20 carbon atoms, substituted-hydrocarbyl radicals containing from 1 to 20 carbon atoms, wherein one or more of the hydrogen atoms is replaced by a halogen atom, or organometalloid radicals wherein each hydrocarbyl substitution in the organo portion contains from 1 to about 20 carbon atoms and said metalloid is selected from the group consisting of silicon; M is a transition metal; "a" and "b" are integers≧0; "c" is an integer≧1; a+b+c=an even-numbered integer from 2 to 8; and "m" is an integer ranging from 5 to 22; "a'" and "b'" are the same or a different integer≧0; "c'" is an integer≧2; a'+b'+c'=an even-numbered integer from 4 to 8; "m'" is an integer from 6 to 12; "n" is an integer such that 2c'−n=d; and "d" is an integer greater than or equal to 1.

32. The composition of matter of claim 31 wherein [A]' is [$(C_2B_9H_{11})_2Co$]'.

33. The composition of claim 28 wherein [A]" is a single anionic coordination complete having a plurality of lipophilic radicals covalently cocoordinated to and shielding a central charge bearing metal or metalloid atom.

34. A process for preparing a catalyst for olefin polymerization comprising:

adding a Group IV-B transition metal component represented by one of the two general formulae

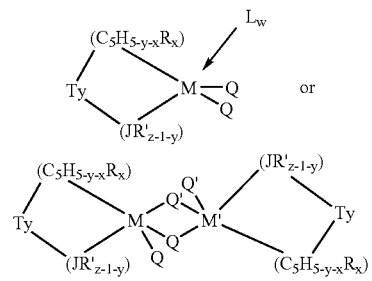

wherein M is Zr, Hf or Ti;

($C_5H_{5-y-x}R_x$) is a cyclopentadienyl ring which is substituted with from zero to five R groups, "x" is 0, 1, 2, 3, 4 or 5 denoting the degree of substitution, and each R group is, independently, a radical selected from the group consisting of $C_1$–$C_{20}$ hydrocarbyl radicals and substituted $C_1$–$C_{20}$ hydrocarbyl radicals, wherein one or more hydrogen atoms are replaced by a halogen atom, $C_1$–$C_{20}$ hydrocarbyl-substituted metalloid radicals wherein the metalloid is selected from the group consisting of germanium and silicon, and halogen radicals; or ($C_5H_{5-y-x}R_x$) is a cyclopentadienyl ring in which two adjacent R groups are joined forming a $C_4$–$C_{20}$ ring to give a saturated or unsaturated polycyclic cyclopentadienyl ligand;

(JR'$_{z-1-y}$) is a heteroatom ligand in which J is an element with a coordination number of three from Group V-A or an element with a coordination number of two from Group VI-A of the Periodic Table of Elements, each R' is, independently, a radical selected from the group consisting of $C_1$–$C_{20}$ hydrocarbyl radicals and substituted $C_1$–$C_{20}$ hydrocarbyl, wherein one or more hydrogen atoms is replaced by a halogen atom, and "z" is the coordination number of the element J;

each Q is, independently, hydride, $C_1$–$C_{20}$ hydrocarbyl radicals and substituted hydrocarbyl radicals, wherein one or more hydrogen atoms is replaced by an electron withdrawing group, or $C_1$–$C_{20}$ hydrocarbyl-substituted metalloid radicals wherein the metalloid is selected from the group consisting of germanium and silicon, provided that Q is not a substituted or unsubstituted cyclopentadienyl ring, or both Q together may be an alkylidene, olefin, acetylene or a cyclometallated hydrocarbyl;

"y" is 0 or 1; when "y" is 1, T is a covalent bridging group containing a Group IV-A or V-A element;

L is a neutral Lewis base; and "w" is a number from 0 to 3; wherein M' has the same meaning as M and Q' has the same meaning as Q;

to an activator component comprising: (1) a cation and (2) a compatible noncoordinating anion.

35. The process of claim 34 wherein the addition of said Group IV-B transition metal component to said activator component is in a diluent.

36. The process of claim 35 wherein the diluent is selected from the group consisting of straight and branched chain hydrocarbons, cyclic and alicyclic hydrocarbons and aromatic and alkyl-substituted aromatic compounds.

37. The process of claim 35 wherein the diluent comprises a liquid olefin.

38. The process of claim 37 wherein the diluent is selected from the group consisting of ethylene, propylene, 1-butene and 1-hexene.

39. The process of claim 35 wherein the activator component is present in the diluent in an amount sufficient to provide a molar ratio of Group IV-B transition metal component to activator component from about 1:10 to about 200:1.

40. The process of claim 34 wherein the activator component is represented by the formula

[(L'-H)⁺]_d[(M')^{m+}Q_1Q_2 ... Q_n]^{d-} wherein
L' is a neutral Lewis base;
H is a hydrogen atom;
(L'-H) is a Bronsted acid;
M' is a metal or metalloid selected from the group consisting of Groups V-B to V-A of the Periodic Table of Elements;
$Q_1$ to $Q_n$ are selected independently from the group consisting of hydride radicals, dialkylamido radicals, alkoxide and aryloxide radicals, hydrocarbyl and substituted-hydrocarbyl radicals and any one, but not more than one of $Q_1$ to $Q_n$ is a halide radical, the remaining $Q_1$ to $Q_n$ being, independently, selected from the foregoing radicals;
m is an integer from 1 to 7;
n is an integer from 2 to 8; and
n−m=d.

41. The process of claim 40 wherein said anion of the activator component is $[B(C_6F_5)_4]^-$.

42. The process of claim 34 wherein the activator component is represented by the formulae

[L'-H]_c[(CX)_a(BX')_mX''_b]^{c-} or [L'-H]_d[[[(CX_3)_a(BX_4)_m(X_5)_b]^{c-}]_2M+]_{d-}
wherein [L'-H] is a cation selected from the group consisting of a H+; an ammonium; a substituted ammonium wherein the substituted ammonium cation has up to three hydrogen atoms replaced with a radical selected from a group consisting of a hydrocarbyl radical containing from 1 to about 20 carbon atoms and a substituted-hydrocarbyl radical containing from 1 to 20 carbon atoms wherein one or more of the hydrogen atoms is replaced by a halogen atom; a phosphonium; and a substituted-phosphonium wherein the substituted phosphonium cation has up to three hydrogen atoms replaced with a radical selected from a group consisting of a hydrocarbyl radical containing from 1 to about 20 carbon atoms and a substituted-hydrocarbyl radical containing from 1 to 20 carbon atoms wherein one or more of the hydrogen atoms is replaced by a halogen atom; C is carbon; B is boron; each of X, X', X'', $X_3$ $X_4$ and $X_5$ are radicals selected, independently, from the group consisting of hydride radicals, halide radicals, hydrocarbyl radicals containing from 1 to about 20 carbon atoms, substituted-hydrocarbyl radicals containing from 1 to 20 carbon atoms wherein one or more of the hydrogen atoms is replaced by a halogen atom, organometalloid radicals wherein each hydrocarbyl substitution in the organo portion contains from 1 to about 20 carbon atoms, and said metalloid is selected from the group consisting of silicon; M is a transition metal; "a" and "b" are integers≧0; "c" is an integer≧1, a+b+c=an even-numbered integer from 2 to 8; and "m" is an integer ranging from 5 to 22; "a'" and "b'" are the same or a different integer≧0; "c'" is an integer≧2; a'+b'+c'=an even-numbered integer from 4 to 8; "m'" is an integer from 6 to 12; "n" is an integer such that 2c'−n=d; and "d" is an integer greater than or equal to 1.

43. The process of claim 34 wherein said anion of the activator component is of a size that said anion is sterically hindered from coordinating to the Group IV-B metal cation, and said anion is labile such that said anion is displaced from said Group IV-B metal cation by an unsaturated hydrocarbon having a Lewis base strength equal to or greater than ethylene.

44. The process of claim 34 wherein said cation of said activator component is a Bronsted acid.

45. The process of claim 34 wherein said cation of said activator component is such that it will irreversibly react with at least one ligand contained in said Group IV-B transition metal component.

46. The process of claim 34 wherein said anion of said activator component is a single anionic coordination complex having a plurality of lipophilic radicals covalently coordinated to and shielding a central charge bearing metal or metalloid atom.

47. A complex, useful as a catalyst for the production of polyolefins, represented by the following general formula:

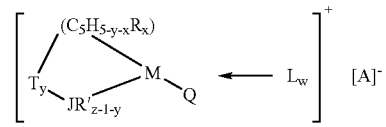

wherein: M is Zr, Hf or Ti;
$(C_5H_{5-y-x}R_x)$ is a cyclopentadienyl ring which is substituted with from zero to five substituent R groups, "x" is 0, 1, 2, 3, 4 or 5 denoting the degree of substitution, and each substituent group R is, independently, a radical selected from the group consisting of methyl, ethyl, propyl, butyl, cyclohexyl, octyl, benzyl, phenyl, trimethylgermyl, trimethylstannyl, triethylplumbyl, trifluoromethyl, trimethylsilyl, triethylsilyl, ethyldimethylsilyl, methyldiethylsilyl, and triphenylgermyl, or $(C_5H_{5-y-x}R_x)$ is a cyclopentadienyl ring in which two adjacent R groups are joined forming an indenyl or tetrahydroindenyl ligand;
(JR'_{z-1-y}) is a heteroatom ligand in which J is an element with a coordination number of three from Group V-A or an element with a coordination number of two from Group VI-A of the Periodic Table of Elements, and each R' is, independently, a radical selected from the group consisting of $C_1$–$C_{20}$ hydrocarbyl radicals and substituted $C_1$–$C_{20}$ hydrocarbyl radicals wherein one or more hydrogen atoms is replaced by a halogen atom, and "z" is the coordination number of the element J;
Q is selected from the group consisting of hydride, methyl, ethyl, propyl, butyl, amyl, hexyl, heptyl, octyl, nonyl, decyl, cetyl, and phenyl;
"y" is 0 or 1; when "y" is 1, T is a linear, branched or cyclic alkylene group having from 1 to 6 carbon atoms or a silylene group having from 1 to 2 silicon atoms;
L is a neutral Lewis base; and "w" is a number from 0 to 3,
[A]⁻ is represented by the formula:

[BAr_1Ar_2X_3X_4]⁻ wherein:
B is boron in a valence state of 3;
$Ar_1$ and $Ar_2$ are each perfluorophenyl; and
$X_3$ and $X_4$ are radicals selected, independently, from the group consisting of hydride radicals, halide radicals, hydrocarbyl radicals containing from 1 to about 20 carbon atoms and substituted-hydrocarbyl radicals con- 48. A complex, useful as a catalyst for the production of polyolefins, comprising the following general formula:

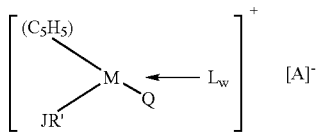

wherein:
M is Zr, Hf or Ti;
J is oxygen;
R' is 2-methylbutyl;
Q is methyl;
w is 1;
L is dimethylphenylamine; and
[A]⁻ is [B(C₆F₅)₄]⁻.

49. A complex, useful as a catalyst for the production of polyolefins, represented by the following general formula:

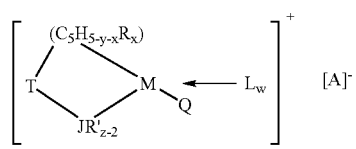

wherein:
M is Zr, Hf or Ti;
(C₅H₄₋ₓRₓ) is a cyclopentadienyl ring which is substituted with from zero to five substituent R groups, "x" is 0, 1, 2, 3 or 4 denoting the degree of substitution, and each substituent group R is, independently, a radical selected from the group consisting of methyl, ethyl, propyl, butyl, cyclohexyl, octyl, benzyl, phenyl, trimethylgermyl, trimethylstannyl, triethylplumbyl, trifluoromethyl, trimethylsilyl, triethylsilyl, ethyldimethylsilyl, methyldiethylsilyl, and triphenylgermyl, or (C5H₄₋ₓRₓ) is a cyclopentadienyl ring in which two adjacent R groups are joined forming an indenyl or tetrahydroindenyl ligand;
(JR'$_{z-2}$) is a heteroatom ligand in which J is an element with a coordination number of three from Group V-A or an element with a coordination number of two from Group VI-A of the Periodic Table of Elements, and R' is a radical selected from the group consisting of C₁–C₂₀ hydrocarbyl radicals and substituted C₁–C₂₀ hydrocarbyl radicals wherein one or more hydrogen atoms is replaced by a halogen atom, and "z" is the coordination number of the element J;
Q is selected from the group consisting of hydride, methyl, ethyl, propyl, butyl, amyl, hexyl, heptyl, octyl, nonyl, decyl, cetyl, and phenyl;
T is a linear, branched or cyclic alkylene group having from 1 to 6 carbon atoms, or a silylene group having from 1 to 2 silicon atoms:
L is a neutral Lewis base, and "w" is a number from 0 to 3;
[A]⁻ is represented by the formula:

$$[BAr_1Ar_2X_3X_4]^-$$

wherein:
B is boron in a valence state of 3;
Ar₁ and Ar₂ are each perfluorophenyl; and
X₃ and X₄ are radicals selected, independently, from the group consisting of hydride radicals, halide radicals, hydrocarbyl radicals containing from 1 to about 20 carbon atoms and substituted-hydrocarbyl radicals containing from 1 to about 20 carbon atoms wherein one or more of the hydrogen atoms is replaced by a halogen atom, provided that X₃ and X₄ are not both halide.

50. A complex, useful as a catalyst for the production of polyolefins, comprising the following general formula:

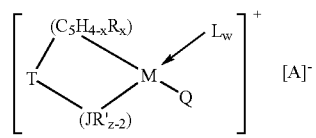

wherein: M is Zr, Hf or Ti,
x is 4,
w is 1;
L is dimethylphenylamine;
each R is methyl;
J is nitrogen;
z is 3;
R' is tert-butyl;
T is dimethylsilyl;
Q is methyl; aid
[A]' is [B(C₆F₅)₄]⁻.

51. A process for preparing a catalyst for polymerization, comprising:
contacting a Group IV-B transition metal component represented by one of the two general formulae

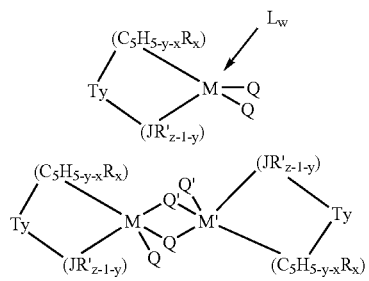

wherein M is Zr, Hf or Ti;
(C₅H$_{5-y-x}$Rₓ) is a cyclopentadienyl ring which is substituted with from zero to five R groups, "x" is 0, 1, 2, 3, 4 or 5 denoting the degree of substitution, and each R group is, independently, a radical selected from the group consisting of methyl, ethyl, propyl, butyl, cyclohexyl, octyl, benzyl, phenyl, trimethylgermyl, trimethylstannyl, triethylplumbyl, trifluoromethyl, trimethylsilyl, triethylsilyl, ethyldimethylsilyl, metiyldietlhylsilyl, and triphenylgermyl, or (C₅H$_{5-y-x}$Rₓ) is a cyclopentadienyl ring in which two adjacent R groups are joined forming an indenyl or tetrahydroindenyl ligand;
(JRK'$_{z-1-y}$) is a heteroatom ligand in which J is an element with a coordination number of three from Group V-A or an clement with a coordination number of two from Group VI-A of the Periodic Table of Elements, and each R' is, radicals and substituted $C_1$–$C_{20}$ hydrocarbyl radicals wherein one or more hydrogen atoms is replaced by a halogen atom, and "z" is the coordination number of the element J;

Q is selected from the group consisting of hydride, methyl, ethyl, propyl, butyl, amyl, hexyl, heptyl, octyl, nonyl, decyl, cetyl, and phenyl;

"y" is 0 or 1; when "y" is 1, T is a linear, branched or cyclic alkylene group having from 1 to 6 carbon atoms, or a silylene group having from 1 to 2 silicon atoms;

L is a neutral Lewis base; and "w" is a number from 0 to 3, wherein M' has the same meaning as M and Q' has the same meaning as Q;

with an activator component represented by the formula:

$$[L'-H]^+[BAr_1Ar_2X_3X_4]'$$

wherein:
L' is a neutral Lewis base;
H is a hydrogen atom;
B is boron in a valence state of 3;
$Ar_1$ and $Ar_2$ are each perfluorophenyl; and
$X_3$ and $X_4$ are radicals selected, independently, from the group consisting of hydride radicals, halide radicals, hydrocarbyl radicals containing from 1 to about 20 carbon atoms and substituted-hydrocarbyl radicals containing from 1 to about 20 carbon atoms wherein one or more of the hydrogen atoms is replaced by a halogen atom, provided that $X_3$ and $X_4$ are not both halide.

52. A process for preparing a catalyst for polymerization, comprising:

contacting a Group IV-B transition metal component represented by the general formula:

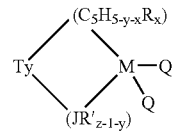

wherein M is Zr, Hf or Ti; x is 4; y is 1; T is dimethylsilyl; each R is methyl, J is nitrogen; z is 3, R' is tert-butyl; and Q is methyl, with an activator component represented by the formula:

$$[L'-H]^+[A]^-$$

wherein L' is dimethylphenylamine. H is a hydrogen atom and $[A]^-$ is $[B(C_6F_5)_4]^-$.

* * * * *